United States Patent [19]

Lattin

[11] 4,031,387
[45] June 21, 1977

[54] METHOD OF DETERMINING WHETHER RADIOACTIVE CONTAMINANTS ARE INSIDE OR OUTSIDE A STRUCTURE

[75] Inventor: Kenneth R. Lattin, Richland, Wash.

[73] Assignee: The United States of America as represented by the United States Energy Research and Development Administration, Washington, D.C.

[22] Filed: Aug. 5, 1976

[21] Appl. No.: 711,926

[52] U.S. Cl. ............................ 250/252; 250/358 R
[51] Int. Cl.² ................. G01D 18/00; G01N 23/00
[58] Field of Search .......... 250/252, 272, 273, 308, 250/358 R

[56] References Cited

UNITED STATES PATENTS 3,955,086   5/1976   Tsujii et al. ................. 250/252 X Primary Examiner—Davis L. Willis
Attorney, Agent, or Firm—Dean E. Carlson; Frank H. Jackson; Donald P. Reynolds

[57] ABSTRACT

A measure is obtained of the relative quantities of radioactive material inside and outside a structure such as a pipe by obtaining two spectra of gamma radiation on a dummy structure of the same shape and composition. A first spectrum is obtained with a quantity of the radioactive element to be measured located inside the structure and a second spectrum is obtained with a quantity of the same contaminant located outside the structure. The two spectra are normalized to the same equivalent value in a portion of the spectrum that does not reflect the presence of gamma rays resulting from Compton scattering in the structure. Comparison of that portion of the spectra obtained where Compton scattering is a factor gives a measure of the relative amounts of contaminants inside and outside the structure on a spectrum obtained from a test structure. The invention may also be practiced by obtaining a plurality of spectra at varying known concentrations inside and outside the dummy structure.

4 Claims, 3 Drawing Figures

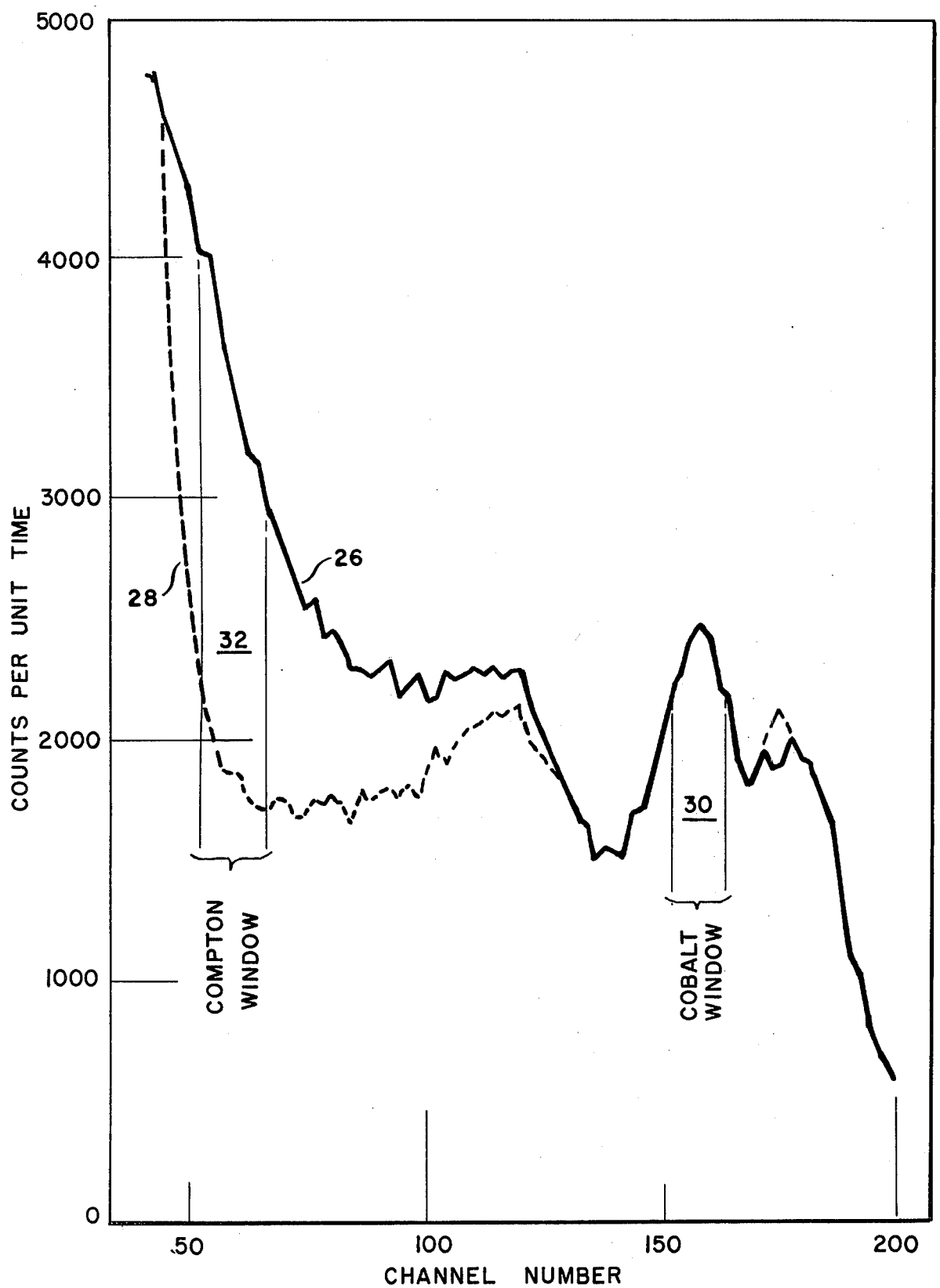

METHOD OF DETERMINING WHETHER RADIOACTIVE CONTAMINANTS ARE INSIDE OR OUTSIDE A STRUCTURE

CONTRACTUAL ORIGIN OF THE INVENTION

The invention described herein was made in the course of, or under, a contract with the UNITED STATES ENERGY RESEARCH AND DEVELOPMENT ADMINISTRATION.

BACKGROUND OF THE INVENTION

This invention relates to a method of determining whether radioactive contaminants are inside or outside a structure, using a detector located outside the structure.

When it becomes necessary for any reason to decontaminate radioactive piping or enclosures, it is necessary to remove radioactive contaminants from wherever they may be. If a structure such as a pipe is found to emit gamma rays that are characteristic of a particular contaminant, it is not always evident whether the contaminant adheres to the inside or the outside of the pipe or, if both, what the relative amounts are. This presents a problem because different techniques are used for cleaning the insides and the outsides of pipes, tubes or other such enclosing structures. One method used in the past for such cleaning operations has been to measure the radioactivity before cleaning, to clean or attempt to clean the outside of the structure, and to make a second measurement of radioactivity so as to determine whether the inside needs to be cleaned as well. This represents a wasted effort if all the measured radioactivity or a substantial portion of it came from radioactive contaminants contained inside the pipe, fittings or valves. Also, inadequate cleaning of the outside of the structure leads to measurements that give a false indication of internal contamination.

Even the method described above may be ineffective unless it is possible to clean or decontaminate a sufficiently large part of the outside portion of a structure in the vicinity of a measuring site to reduce the interfering effect of stray external radiation. In addition, there are conditions under which the difficulty of access to portions of a reactor during diassembly may make it difficult or impossible to decontaminate enough area around the measuring site to avoid the masking effect of radiation from surrounding external surfaces in view of the fact that radiation passing through a tube or valve is attenuated by the material of the tube or valve.

It is an object of the present invention to provide a better method of measuring the relative quantities of radioactive contaminants inside and outside a structure.

It is a further object of the present invention to provide a method for measuring the relative amounts of radioactive contaminants present inside and outside a structure without performing a preliminary decontamination.

Other objects will become apparent in the course of a detailed description of the invention.

SUMMARY OF THE INVENTION

A measure of the relative quantities of a known radioactive contaminant inside and outside a given structure is obtained by placing a known quantity of the contaminant inside a dummy structure of the same shape and material as the test structure, obtaining a gamma spectrum from outside the dummy structure, then removing the first radioactive contaminant from inside and placing a sample of the radioactive contaminant outside. A second gamma spectrum is then obtained and the two spectra are normalized to comparable values in a region of the spectra in which Compton scattering is not significant. A gamma spectrum of the test structure is measured and normalized to compare with the other spectra in the region where Compton scattering is not a factor. The three spectra are compared in a region in which Compton scattering is a factor. The establishment of a calibration between radiation from inside the dummy structure with radiation from outside the dummy structure provides a measure of the relative amount of contamination inside and outside the test structure.

BRIEF DESCRIPTION OF THE DRAWINGS

FIG. 2 is a set of spectra from a test specimen.

DETAILED DESCRIPTION OF THE INVENTION

Figure 1:
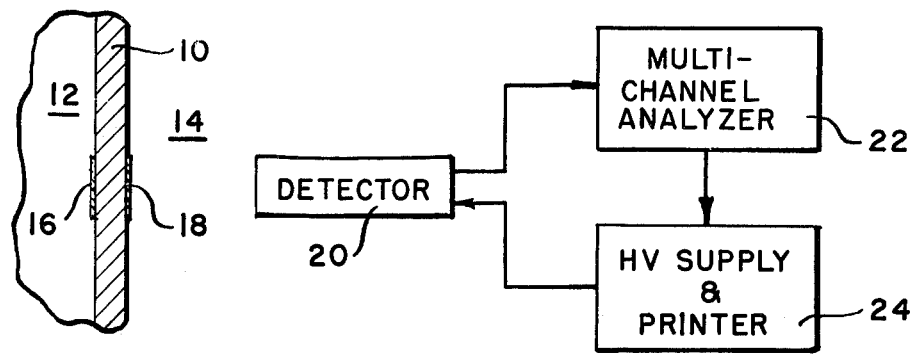
FIG. 1 is a schematic block diagram of a setup for determining radiation spectra.

FIG. 1 is a schematic block diagram of a typical setup for measuring contamination. In FIG. 1, wall 10 represents a portion of a typical structure such as a pipe or tube that has an inside 12 and an outside 14. Internal source 16 represents a quantity of a known radioactive material that is located inside wall 10 and external source 18 represents a source of the same radioactive material that is located outside wall 10. Detector 20 is placed in measuring proximity to wall 10 at a location such that detector 20 is responsive to radiation from internal source 16 and external source 18. The precise form of detector 20 will vary with the particular radioactive material that is to be detected. A detector 20 is selected that generates detectable signals in response to the radiation that is present. The signals are coupled to multichannel analyzer 22 and a spectrum of radiation is thereby obtained and printed on high-voltage supply and printer 24.

Operation of the setup of FIG. 1 to practice the present invention proceeds as follows. A quantity of the known radioactive material to be measured is placed to serve as an internal source 16 within wall 10 of a dummy of the structure to be measured. Detector 20 is placed in measuring proximity to wall 10 and a spectrum of radiation is obtained on multichannel analyzer 22 and high-voltage supply and printer 24. This spectrum represents radiation detected through wall 10 from internal source 16. Internal source 16 is then removed and external source 18 is placed to provide a measuring sample of the same radioactive material as that used formerly for internal source 16. A second spectrum is now obtained by placing detector 20 in measuring proximity to external source 18. The two spectra will in general be different in two ways. First, their amplitudes will differ throughout all or almost all of the measuring region. Second, in a portion of the spectrum, to be defined later as the Compton window, the spectra differ from one another on a relative basis. These differences will be made clear by reference to FIGS. 2 and 3.

FIG. 2 is a plot of two spectra of gamma radiation that were obtained using the test setup of FIG. 1. Spectrum 26 was obtained with an internal source of cobalt 60 and no external source and will be referred to as an internal spectrum. Spectrum 28 was obtained with an external source of cobalt 60 and no internal source and will be referred to as an external spectrum. Each such spectrum is a plot of the counts per minute of radioactive disintegrations plotted as a function of the channel number in the multichannel analyzer 22 of FIG. 1. The channel number is a relative measure of the energy of detected gamma rays. Gamma energy increases with increasing channel numbers. As orginally obtained, spectrum 26 differed throughout in height from spectrum 28. The two spectra were normalized for comparison by referring to the values in cobalt window 30. Cobalt window 30 is so defined because it is a region of the two spectra in which Compton scattering is not detectable in the spectrum. The cobalt window is accordingly selected as a basis for normalizing the two spectra to the same relative heights and this has been done in FIG. 2. It can be seen that the two spectra then diverge in the left-hand portion of FIG. 2 and in particular are divergent in a region of the curve that is referred to as Compton window 32. This is a portion of the spectrum in which Compton scattering in the wall has altered the spectrum. With spectrum 26 representing entirely contamination or radiation from an internal source and spectrum 28 representing entirely contamination or radiation from an external source, a spectrum on a sample that is similar in composition and geometry to the test sample that has been normalized to the same cobalt window 30 will produce a spectrum in Compton window 32 that can be scaled linearly to give a relative measure of how much of the contamination is inside and how much is outside. The spectrum of FIG. 2 was obtained using a test sample of carbon steel 0.25 inch thick. The detector was a 3 inch ×3 inch sodium iodide crystal that was connected to a TMC 402 multichannel analyzer.

Figure 3:
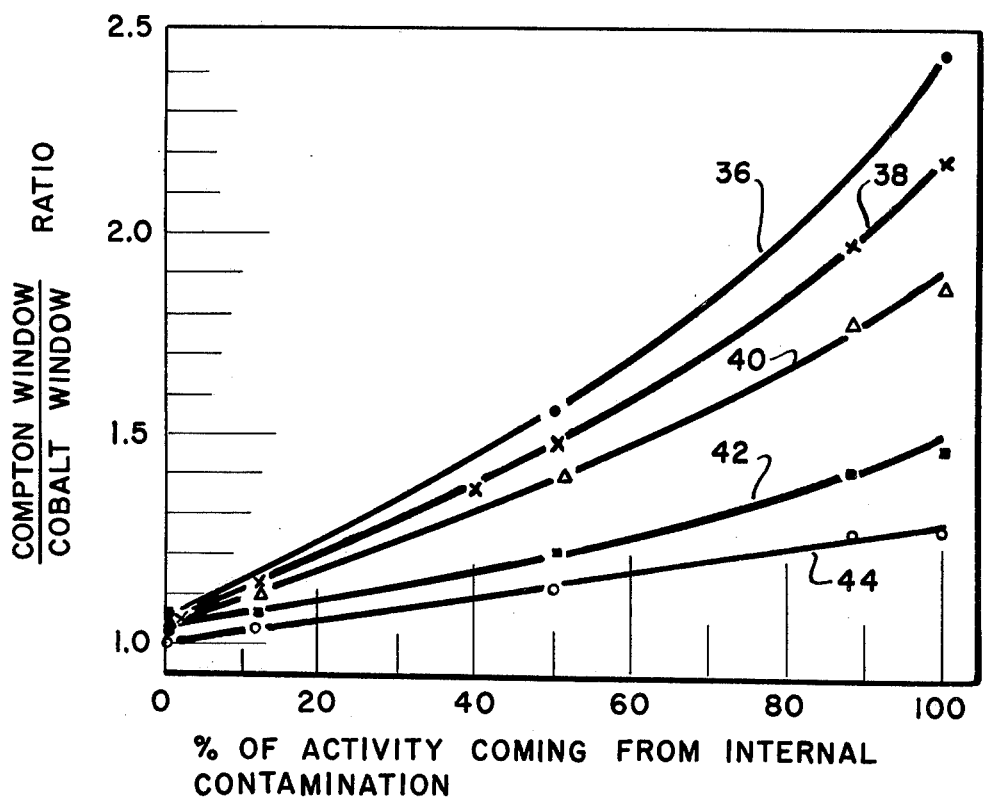
FIG. 3 is a plot of the ratios of Compton to cobalt scattering as a function of the percentage of activity that comes from internal contamination.

Comparative results obtained on various samples are shown in FIG. 3 which is a plot of the ratio of counts in the Compton window to counts in the cobalt window. With reference to FIG. 2, this represents a ratio of the area in Compton window 32 under the particular spectrum to the area in cobalt window 30. FIG. 2 includes points taken at five relative levels of contamination on five different samples. This demonstrates the approximate linearity of the curves and also provides for a measure with increased accuracy if desired. The abscissa of the curve in FIG. 3 is the percent of activity coming from internal contamination as a function of the total amount of contamination. Points were taken by placing measured amounts of radioactive material, in this case cobalt 60, both inside and outside each of the various test structures and making the measurements described above. In FIG. 3, curve 36 represents points taken on a test sample of carbon steel 0.500 inch in thickness. Curve 38 represents points taken on a sample of carbon steel 0.400 inch in thickness. Curve 40 represents points obtained on a sample of carbon steel 0.250 inch in thickness. Curve 42 represents a test structure of carbon steel 0.125 inch in thickness. Curve 44 represents a test structure of aluminum 0.190 inch in thickness. The Compton window for all the measurements that are summarized in Table III was taken as the range of energies from 0.33 to 0.53 MeV, and the cobalt window was 1.13 to 1.21 MeV. Curve 36 was obtained with points representing all internal contamination, 50% internal contamination, and 0 internal contamination. All the other curves in FIG. 3 were obtained using samples representing the following percentages of activity resulting from internal contamination: 0, 14, 50, 86, and 100%. Curve 38 also includes one point at 40 internal contamination. Each of the curves 36 through 44 serves as a measure to relate an observed ratio of activity from a Compton window to activity from a cobalt window to a corresponding percentage of internal contamination as achieved on a test piece that corresponds in structure, dimensions and materials to the appropriate curve in FIG. 3. For purposes of decontamination, the straight lines passing through the end points of each curve will ordinarily provide enough accuracy.

The foregoing results have been illustrated using radioactive cobalt 60 as the contaminant of concern. This was done because cobalt 60 is likely to be the subject of intensive effort in decontamination of any materials containing cobalt that have been exposed to a flux of neutrons. Pipe scale that has circulated through a reactor core is a typical object of such decontamination. However, the teachings herein can be equally as well applied to any radioactive material that produces radiation that leads to Compton scattering in one portion of a spectrum and in which Compton scattering is negligible in another portion of the spectrum. In such a case, a standardizing window is selected in the portion of the spectrum in which Compton scattering is not a factor. This window is used to normalize spectra from internal and external contamination on a dummy structure. A comparison is then made of the radiation through the Compton window as shown herein. This comparison then leads to the development of calibration curves for particular dummy samples and particular contaminants, just as those of FIG. 3 were obtained for radioactive cobalt 60 in the materials and the dimensions shown in FIG. 3.

The embodiments of the invention in which an exclusive property of privilege is claimed are defined as follows:

1. A method of determining the amount of radioactive material inside a test structure compared to the amount outside the structure comprising the steps of:
   a. disposing a first quantity of the radioactive material inside a dummy structure having the same shape and made of the same material as the test structure;
   b. obtaining an inside spectrum of radiation from the first quantity of material inside the dummy structure by detecting radiation outside the dummy structure over a test range of energies that includes a Compton window where Compton scattering is caused by the material and that also includes a region of the spectrum where Compton scattering is negligible;
   c. removing the first quantity;
   d. disposing a second quantity of the radioactive material outside the dummy structure;
   e. obtaining an outside spectrum of radiation from the second quantity by detecting radiation outside the dummy structure over the test range of energies;
   f. obtaining a test spectrum from the test structure by detecting radiation outside the test structure over the test range of energies;
   g. obtaining from the inside spectrum and outside spectrum ratios of counts of radioactive disintegrations per unit time in the Compton window to counts of radioactive disintegrations per unit time in the region where Compton scattering is negligible;

h. obtaining from the test spectrum a test ratio of counts of radioactive disintegrations per unit time in the Compton window to counts of radioactive disintegrations per unit time in the region where Compton scattering is negligible;

i. comparing the test ratio linearly with the ratio from the inside spectrum and the ratio from the outside spectrum to obtain a proportional measure, which proportional measure is a measure of the amount of the radioactive material inside the test structure compared to the amount outside.

2. A method of determining the percentages of pipe scale containing radioactive cobalt 60 that are located inside and outside a test pipe, the method comprising the steps of:

a. disposing a first quantity of cobalt 60 inside a dummy pipe having the same composition and structure as the test pipe;
  b. measuring gamma radiation outside the dummy pipe from the cobalt 60 inside the dummy pipe over a range of energies including values between 0.33 MeV and 1.21 MeV;
  c. disposing a second quantity of cobalt 60 outside the dummy pipe;
  d. measuring gamma radiation outside the dummy pipe from the cobalt 60 outside the dummy pipe over the range of energies;
  e. measuring gamma radiation outside the test pipe over the range of energies;
  f. calculating ratios of energy in a Compton window to energy in a cobalt window for the measurements of steps (b), (d), and (e);
  g. comparing the ratios to determine a percentage of cobalt 60 that is inside the test pipe and a percentage that is outside the test pipe.

3. The method of claim 2 wherein the Compton window is the range of energies between 0.33 and 0.53 MeV and wherein the cobalt window is the range of energies between 1.13 and 1.21 MeV.

4. The method of claim 2 wherein the step of comparing the ratios comprises the steps of:

a. plotting on a graph of the ratio of energy in the Compton window to energy in the cobalt window vs. percent of activity from internal contamination a first point representing the measurement of radiation from cobalt 60 inside the dummy pipe and a second point representing the measurement of radiation from cobalt 60 outside the dummy pipe;
  b. connecting the first and second points with a straight line.
  c. marking a third point on the straight line at a value equal to the ratio of energy in the Compton window to energy in the cobalt window for the measurement of gamma radiation outside the test pipe;
  d. reading a value of percent of activity from internal contamination corresponding to the third point, which value is the percentage of cobalt 60 inside the test pipe.

* * * * *